United States Patent
Moutinho Colunas et al.

(10) Patent No.: US 12,318,192 B2
(45) Date of Patent: Jun. 3, 2025

(54) DETECTION OF ENVIRONMENT FOR VOICE CONTROL OF MOTION TRACKING SYSTEM

(71) Applicant: SWORD HEALTH S.A., Oporto (PT)

(72) Inventors: Márcio Filipe Moutinho Colunas, Oporto (PT); Luís António Correia De Oliveira, Oporto (PT); José Carlos Coelho Alves, Oporto (PT); Rui Xavier Fialho Costa, Oporto (PT); Virgílio António Ferro Bento, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 603 days.

(21) Appl. No.: 17/789,763

(22) PCT Filed: Dec. 23, 2020

(86) PCT No.: PCT/EP2020/087785
§ 371 (c)(1),
(2) Date: Jun. 28, 2022

(87) PCT Pub. No.: WO2021/130324
PCT Pub. Date: Jul. 1, 2021

(65) Prior Publication Data
US 2023/0043643 A1    Feb. 9, 2023

(30) Foreign Application Priority Data
Dec. 23, 2019 (EP) ..................................... 19398018

(51) Int. Cl.
*A61B 5/11* (2006.01)
*A61B 5/00* (2006.01)
*G06F 3/16* (2006.01)

(52) U.S. Cl.
CPC .......... *A61B 5/1118* (2013.01); *A61B 5/0022* (2013.01); *A61B 5/0024* (2013.01); *A61B 5/749* (2013.01); *G06F 3/167* (2013.01)

(58) Field of Classification Search
CPC ... A61B 5/0022; A61B 5/1118; A61B 5/0024; A61B 5/749; A61B 2505/09; G06F 3/167
See application file for complete search history.

(56) References Cited

U.S. PATENT DOCUMENTS

| | | | |
|---|---|---|---|
| 9,773,401 B1* | 9/2017 | Auvenshine | ............ H04W 4/38 |
| 2015/0196804 A1* | 7/2015 | Koduri | ............... G06Q 10/0639 |
| | | | 482/8 |

(Continued)

FOREIGN PATENT DOCUMENTS

| | | |
|---|---|---|
| EP | 3816772 A1 | 5/2021 |
| EP | 3842922 | 6/2021 |

(Continued)

OTHER PUBLICATIONS

EP Application No. 19398018.2 Extended European Search Report dated Jun. 23, 2020.

(Continued)

*Primary Examiner* — Vincent H Tran
(74) *Attorney, Agent, or Firm* — SCHWEGMAN LUNDBERG & WOESSNER, P.A.

(57) ABSTRACT

A method for allowing or disallowing control of a motion tracking system by means of voice, comprising: digitally processing sound detected by each microphone of the at least one microphone; digitally computing SNR by computing both first energy of a voice signal in the detected sound and second energy of noise in the detected sound; digitally processing electromagnetic waves captured by each antenna of the at least one antenna so as to detect data packets transmitted to the computing apparatus by each sensor of the plurality of sensors, each data packet including RSSI of a (Continued)

respective sensor; digitally computing distance between each sensor and the computing apparatus based on the RSSI of the data packets received from the respective sensor; digitally computing a percentage of sensors of the plurality of sensors having at least one of: a distance exceeding a predetermined maximum distance threshold, and a change in distance exceeding a predetermined maximum changing distance threshold; and digitally setting allowance or disallowance of voice control based on both the SNR computed and the percentage of sensors computed.

15 Claims, 3 Drawing Sheets

(56) References Cited

U.S. PATENT DOCUMENTS

| | | | | |
|---|---|---|---|---|
| 2016/0335876 | A1* | 11/2016 | Verma | G01S 11/06 |
| 2017/0296873 | A1* | 10/2017 | Kitamura | H04Q 9/00 |
| 2017/0333752 | A1* | 11/2017 | Korkala | A61B 5/02416 |
| 2018/0070864 | A1* | 3/2018 | Schuster | G16H 40/63 |
| 2018/0126241 | A1 | 5/2018 | Hung et al. | |
| 2018/0376284 | A1 | 12/2018 | Soro et al. | |
| 2019/0206396 | A1* | 7/2019 | Chen | G06F 3/167 |
| 2019/0283247 | A1* | 9/2019 | Chang | A61B 5/1121 |

FOREIGN PATENT DOCUMENTS

| | | |
|---|---|---|
| EP | 4081895 | 11/2022 |
| WO | WO-2019243438 A1 | 12/2019 |
| WO | WO-2021130324 A1 | 7/2021 |

OTHER PUBLICATIONS

PCT/EP2020/087785 International Search Report and Written Opinion dated Mar. 24, 2021.

"International Application Serial No. PCT EP2020 087785, International Preliminary Report on Patentability mailed Jul. 7, 2022", 16 pgs.

"European Application Serial No. 19398018.2, Noting of loss of rights pursuant to Rule 112(1) EPC mailed Feb. 7, 2022", 2 pgs.

"European Application Serial No. 20833912.7, Response to Communication pursuant to Rules 161(1) and 162 EPC filed Feb. 3, 2023", 8 pgs.

"European Application Serial No. 20833912.7, Noting of loss of rights pursuant to Rule 112(1) EPC mailed Jul. 19, 2024", 1 pg.

* cited by examiner

DETECTION OF ENVIRONMENT FOR VOICE CONTROL OF MOTION TRACKING SYSTEM

CROSS-REFERENCE TO RELATED APPLICATIONS

This application is a U.S. National Entry Application of International Application No. PCT/EP2020/087785, filed on Dec. 23, 2020, which claims the benefit of European Application Serial No. 19398018.2, filed on Dec. 23, 2019, all of which are incorporated by reference in their entireties.

TECHNICAL FIELD

The present invention relates to the technical field of motion tracking systems. More particularly, the present invention relates to determining whether voice control of a motion tracking system is possible or not depending upon the noise present in the environment and the situation of the user of the motion tracking system.

STATE OF THE ART

Motion tracking or motion capture of a target is a technical process used in many applications, such as, control of machines, automatization of processes, or gait analysis to name a few. The motion of a person or an object can be tracked by means of sensors that are attached to the person or object.

In some applications in which the motion of a person is tracked, it is important that the person is able to control the motion tracking system for correct operation thereof. The person starts the motion tracking procedure, pauses it, resumes it, stops it, triggers a calibration routine whereby the sensors of the motion tracking systems are to be calibrated or recalibrated, etc.

Further, the motion sequence provided by a computing apparatus of the motion tracking system is processed in accordance with the concerned application. For instance, personal physical exercise and physical rehabilitation are applications that may rely on motion tracking and which are becoming more and more popular. As disclosed in international application no. PCT/EP2019/066237, a person may train or do physical therapy at some premises (e.g. at home, at a clinic) without the direct supervision of a trainer or a therapist, for example, yet the user is able to review her/his own physical exercises or provide information about the same to the trainer or the therapist, thanks to motion tracking. In such application, the person may also control the operation of the motion tracking system such that the physical exercises are started, paused, skipped, the difficulty thereof adjusted, etc.

As described in commonly owned European patent application EP19398014.1, which is incorporated herein by reference in its entirety, the user of the motion tracking system is able to control the system by way of voice commands. Such type of control is desirable since oftentimes the user is at a distance from the computing apparatus that manages the operation of the motion tracking procedure so that she/he has sufficient room for doing the physical exercises, and thus reaching user input means may not be possible in some occasions, or it would cause the training or exercising to be cumbersome.

However, for voice control to be effective, the level of noise in the environment cannot be excessive, otherwise the voice commands become muffled owing to the noise, and the computing apparatus cannot determine whether a voice command has been received and, if received, which voice command it is. Accordingly, there is an interest in determining whether the environment is in proper condition for voice control of the motion tracking system and whether the user is able to reach user input means or not so that voice control is enabled or disabled, thereby reducing the likelihood of the computing apparatus changing the operation of the motion tracking system incorrectly.

DESCRIPTION OF THE INVENTION

A first aspect of the invention relates to a method for allowing or disallowing control of a motion tracking system by means of voice, the motion tracking system comprising a plurality of sensors adapted for arrangement on a body of a user and configured to wirelessly transmit data packets, and a computing apparatus comprising both at least one antenna and at least one microphone, the method comprising:
  digitally processing, with the computing apparatus, sound detected by each microphone of the at least one microphone;
  digitally computing, with the computing apparatus, a signal-to-noise ratio (i.e. SNR) by computing both first energy of a voice signal in the detected sound and second energy of noise in the detected sound;
  digitally processing, with the computing apparatus, electromagnetic waves captured by each antenna of the at least one antenna so as to detect data packets transmitted to the computing apparatus by each sensor of the plurality of sensors, each data packet including both a received signal strength indicator (i.e. RSSI) and one or more measurements of a respective sensor;
  digitally computing, with the computing apparatus, distance between each sensor and the computing apparatus based on the RSSI of the data packets received from the respective sensor;
  digitally computing, with the computing apparatus, a percentage of sensors of the plurality of sensors having at least one of: a distance exceeding a predetermined maximum distance threshold (e.g. max_dist), and a change in distance exceeding a predetermined maximum changing distance threshold (e.g. max_change_dist); and
  digitally setting, in the computing apparatus, allowance or disallowance of voice control based on both the SNR computed and the percentage of sensors computed.

For deciding and setting whether voice control is to be enabled or disabled, the computing apparatus at least considers the signal-to-noise ratio computed based on the sound detected, and the distance or change in distance computed based on the RSSI values provided by the different sensors. The signal-to-noise ratio establishes whether the environment is noise-free enough to detect voice commands and determine which voice commands are, whereas the distance values may be indicative of the level of noise in the environment in addition to being indicative of the distance between the user and the computing apparatus.

The at least one microphone captures the sound of the environment and any voice command that the user may have provided. Upon processing the captured sound, the computing apparatus computes a signal-to-noise by assuming that sound with certain characteristics (e.g. high energy, given frequencies, etc.) belong to voice (which is the signal) and that sound with some other characteristics (e.g. low energy, given frequencies, etc.) belong to noise. Thus, making these assumptions, the computing apparatus provides an SNR value that indicates how noisy the environment is with respect to any voice or voices captured by the at least one microphone. In this sense, the voice or voices captured could not belong to the user of the motion tracking system, even though the computing apparatus may be configured to carry out a procedure as described in commonly owned European patent application EP19398014.1 for determining whether a given voice belongs to the user or not.

Further, based on the RSSI measurements that each sensor provides within the data packets (in addition to the one or more measurements of the sensor itself, which are then used by the computing apparatus during the motion tracking procedure to determine a motion tracking sequence of the tracked person or object), the computing apparatus estimates the distance between each sensor and the computing apparatus. The sensors may use a communication protocol that provides RSSI values, for example different versions of Bluetooth incorporate the provision of RSSI values. For a more accurate distance computation, a calibration procedure preferably takes place before use of the motion tracking system or from time to time so that the computing apparatus has data about the power with which the electromagnetic waves are expected to be received when the sensors are at a certain distance, and by means of the RSSI values the computing apparatus estimates the distance of each sensor to the computing apparatus.

The RSSI values that each sensor provides are indicative of strength with which the respective sensor receives wireless signals from the computing apparatus, hence their value depends on the intensity with which the sensor receives electromagnetic waves radiated by the computing apparatus. The sensors capture electromagnetic waves radiated by the computing apparatus when there is a wireless communications link established between the computing apparatus and the respective sensor, and/or when there is not such wireless communications link in place (e.g. when broadcast messages are transmitted by the computing apparatus, when messages are transmitted by the computing apparatus to other sensors, etc.).

Since for providing a motion tracking sequence of a person or an object a plurality of moving parts thereof is necessary (motion of a single reference point only shows the movement of the target, not parts thereof), at least a plurality of sensors need to be arranged on the person or object. Accordingly, in order to minimize the number of cases in which one sensor out of the plurality may result in the change of allowance or disallowance of voice control, the percentage of sensors fulfilling a predetermined criterion is computed, hence the percentage of sensors is used for setting allowance or disallowance of the voice control. In this respect, preferably data packets of all the sensors are processed so that, based on the resulting RSSI values thereof and the computed distances, it can be determined (or ruled out) whether a change in RSSI (and, thus, in computed distance) could be due to a temporal problem, like for example an interference in the transmission of the electromagnetic wave, or reflection thereof, or occlusion thereof, etc.

The predetermined criterion is that the calculated distance for a respective sensor exceeds max_dist, and/or that the distance during a time period has changed more than max_change_dist. Concerning the latter, the computing apparatus computes the distance of the respective sensor for the different RSSI values as the data packets of the sensor are processed by the computing apparatus, and establishes whether the distance corresponding to two data packets that have arrived at the computing apparatus at first and second time instants results in an increase in distance exceeding max_change_dist. The difference in time between the first and second time instants (indicated in form of timestamps) must be such that is equal to or less than a predetermined maximum distance time threshold (e.g. max_change_dist_time).

In order to avoid spontaneous communications problems that may occur from time to time and due to which the distance values computed may significantly change, instead of comparing the distance or the change in distance with thresholds, mean distances and changes in mean distances can be computed and compared with thresholds. In this sense, the mean distance is an average computed by the computing apparatus from the distance values computed for each sensor in a period of time, and the change in mean distance is the difference between two mean distance values computed for each sensor at two different time instants.

Based on the calculated SNR value (or values, when the procedure is repeated over time) and percentage of sensors fulfilling any one of the criteria, from which it can be derived how good or bad is the environment for voice control, the computing apparatus enables or disables the voice control.

In the context of the present disclosure, "periods of time" and "time intervals" encompass the data packets or electromagnetic waves received by the computing apparatus at time instants that fall within the period of time or time interval under evaluation. In this sense, it is noted that the data packets are discrete and received at different times, thus the discrete nature of the data packets is considered for calculating, for example, mean distances.

In some embodiments, the step of digitally setting allowance or disallowance comprises: allowing voice control when both the SNR computed exceeds a predetermined minimum SNR threshold (e.g. min_SNR) and the percentage of sensors computed does not exceed a predetermined maximum distant sensors threshold (e.g. max_sensor_perc); and disallowing voice control when the SNR computed does not exceed the predetermined minimum SNR threshold (e.g. min_SNR) or the percentage of sensors computed exceeds the predetermined maximum distant sensors threshold (e.g. max_sensor_perc).

Both the SNR and the percentage of sensors must fulfill the corresponding thresholds in order for the computing apparatus to allow voice control, else the computing apparatus disallows voice control if at least one of the SNR and the percentage of sensors does not fulfill the respective threshold. In this way, the most conservative approach is taken whereby voice control cannot be used by the user of the motion tracking system if the SNR is not sufficient or the distance values computed based on the RSSI values are indicative of an excessive distance or increase in the distance between the user and the computing apparatus.

In some embodiments, the distance between each sensor and the computing apparatus digitally computed is a mean distance between each sensor and the computing apparatus in a time interval having a duration between a predetermined minimum distance time threshold (e.g. min_distance_time) and a predetermined maximum distance time threshold (e.g. max_distance_time).

As aforementioned, the mean distance can be used for avoiding false positives due to sporadic problems, for example an interference that occurs during few tenths of a second, a person walking by that during a short period of time (e.g. half a second, one second, or more) between the user and the computing apparatus, etc. It has been found out that the use of mean distances provides better results when it comes to reliability of enabling or disabling the voice control in non-controlled environments such as, for example but without limitation, a room where multiple users are performing rehabilitation exercises.

The averaging of the computed distances is done such that the mean distance is computed within a time interval that at least lasts min_distance_time but does not last more than max_distance_time. The selection of the minimum and maximum thresholds may be based on experimental tests, and be dependable upon the apparent characteristics of the premises and the environment. Again, the time interval is defined so as to encompass data packets with arrival timestamps falling within a given time interval under evaluation.

In some embodiments, the percentage of sensors is a ratio of A divided by B, where A is a number of sensors whose computed mean distance has increased more than a predetermined maximum mean distance change threshold (e.g. max_mean_distance_threshold) in a time interval having a duration between a predetermined minimum mean distance time threshold (e.g. min_mean_distance_time) and a predetermined maximum mean distance time threshold (e.g. max_mean_distance_time), and B is a total number of sensors in the plurality of sensors.

The change in distance may also be computed as change in mean distance as aforementioned, this again providing more reliable performance of the motion tracking system when determining whether voice control is possible or not.

In some embodiments, the computed distance between a sensor and the computing apparatus is either equal to or proportional to $$10^{\frac{Pmeasured-RSSImean}{10 \cdot K}}.$$

Pmeasured is a predetermined value corresponding to expected power with which an antenna captures electromagnetic waves of the sensors at a predetermined distance value from the computing apparatus. This value is preferably calibrated from time to time so that the distance calculations of the computing apparatus are more accurate and take into account any changes in the radiation power of the different sensors. The radiation power usually variates in accordance with the amount of energy stored in the battery of each sensor; also, the electronics of the sensor change during the operating life thereof, thus the radiation power also changes. Also, the power reception set by Pmeasured also takes into account the reception capacity of the at least one antenna of the computing apparatus and electronics thereof, thus the calibration of this parameter also takes into account the changes experienced by the computing apparatus during the operating life thereof.

RSSImean is a mean RSSI of the corresponding sensor. In particular, the different RSSI provided by each sensor in the data packets thereof are processed by the computing apparatus and a mean RSSI is provided.

K is a predetermined value corresponding to a factor of wave propagation in an environment where the motion tracking system is located. This value can be manually adjusted based on experimental tests. The more accurate the K value is, the more accurate the distance computations may be.

The mean RSSI is preferably computed by averaging RSSI values of data packets of a same sensor that arrive within a time interval having a duration between a predetermined minimum RSSI time threshold (e.g. min_RSSI_time) and a predetermined maximum RSSI time threshold (e.g. max_RSSI_time). When mean distances are computed, preferably the predetermined minimum RSSI time threshold is equal to the predetermined minimum distance time threshold (e.g. min_distance_time) and the predetermined maximum RSSI time threshold is equal to the predetermined maximum distance time threshold (e.g. max_distance_time), that is to say, min_RSSI_time=min_distance_time, and max_RSSI_time=max_distance_time.

As it is readily apparent, the skilled person can perform the distance computation with other formulas aside from the one above without departing from the scope of the present invention.

In some embodiments, the step of digitally computing the SNR comprises: providing a plurality of windows, each window comprising a different fragment of sound detected; computing energy of the sound in each window of the plurality of windows; setting a maximum energy value with the highest computed energy; discarding the window or windows of the plurality of windows having energy less than a predetermined percentage of the highest computed energy; and computing the first energy based on the non-discarded windows of the plurality of windows, and the second energy based on the discarded windows of the plurality of windows.

The computing apparatus assumes that windows having a high computed energy correspond to windows having voice therein, whereas windows having a low computed energy correspond to windows not having voice therein. Accordingly, the computing apparatus first produces all the windows which are fragments from a stream of sound detected by the at least one microphone, which has a duration of e.g. half a second, one second, two seconds, etc. The windows preferably have a duration between 20 and 50 ms (the endpoints being included), and more preferably have a duration of, for example, 25 ms, 30 ms, 35 ms, and preferably each window has a same time duration. The windows are short in duration because speech is typically quasi-stationary, thus windows of such duration can capture speech. Also, owing to both the particularities of speech and the duration of these windows, by computing energy of the windows, especially those with highest energy, it can be determined the energy of speech, that is to say, the signal in the signal-to-noise ratio.

The computing apparatus processes all the windows in order to compute the energy thereof and find the window with highest energy. The highest energy is then used for determining which windows have noise as sound, and these windows are the ones with energy that is less than the predetermined percentage (e.g. 45%, 55%, 65%, etc.) of said highest energy. The windows with noise are discarded for purposes of computing the first energy (of the signal), but are used for computing the second energy (of the noise). Then, the computing apparatus computes the SNR.

In some embodiments, the step of digitally computing the SNR comprises: transforming the sound detected into a frequency domain; computing the first energy of the sound detected for frequencies within a frequency range associated with human voice (e.g. a frequency range between 0.3 kHz and 3.4 kHz or 4 kHz, etc.); and computing the second energy of the sound detected for frequencies different from the frequency range associated with human voice (e.g. one or more frequencies between 0 Hz and 0.3 kHz; 4 kHz and 10 kHz; 4 kHz and 15 kHz, etc.).

The transformation of the sound into the frequency domain is preferably made by applying a Fast Fourier Transform (i.e. FFT) to the detected sound. Then, from the resulting frequency spectrum, the first energy and second energy are computed by selecting the frequency ranges for signal (that is to say, speech) and noise.

In some embodiments, the step of digitally computing the SNR comprises: applying at least a first digital filter to the sound detected thereby providing a first filtered sound, the first digital filter being a bandpass filter for frequencies of a frequency range associated with human voice (e.g. a frequency range between 0.3 kHz and 3.4 kHz or 4 kHz, etc.); applying at least a second digital filter to the sound detected thereby providing a second filtered sound, the second digital filter at least filtering out frequencies of the frequency range associated with human voice; and computing the first energy from the first filtered sound and the second energy from the second filtered sound.

In some embodiments, the step of digitally computing distance between each sensor and the computing apparatus based on the RSSI of the data packets received from the respective sensor comprises establishing the distance according to the RSSI of the data packets.

In order to reduce computational burden and, thus, the power consumption, the computation of the distance (or of any one of: the change in distance, the mean distance and the change in mean distance) is only based on the RSSI values such that the distance is inversely proportional to the RSSI. Accordingly, the RSSI is measured such that the greater the RSSI value is, the lower the distance that will be computed, and the lower the RSSI value is, the greater the distance that will be computed.

In some embodiments, the method further comprises repeating the digital steps with the computing apparatus one or more times for digitally setting allowance or disallowance of voice control in accordance with both most recent sound detection and most recent electromagnetic wave capture (and, thus, most recent data packets).

The process is repeated so that, during a time period or the complete duration of the motion tracking procedure, the voice control may be enabled and disabled multiple times based on the most recent characteristics of the environments and the distance between the user and the computing apparatus. By way of example, during a period of e.g. five minutes, the conditions of the environment or the user may change considerably several times and, hence, voice control is only allowed at certain times during said period.

In some embodiments, the step of digitally setting allowance or disallowance is further based on a predetermined flag corresponding to a physical exercise to be carried out by the user such that: when the predetermined flag is indicative of the user not being within reach of the computing apparatus during performance of the physical exercise, the computing apparatus digitally sets allowance of voice control irrespective of both the SNR computed and the percentage of sensors computed; and when the predetermined flag is indicative of the user being within reach of the computing apparatus during performance of the physical exercise, the computing apparatus digitally sets allowance or disallowance based on both the SNR computed and the percentage of sensors computed.

The predetermined flag can be enabled or not during operation of the motion tracking system, and while enabled, it can override the criteria (SNR and percentage of sensors) for establishing whether voice control must be enabled or disabled.

When the motion tracking system is used for rehabilitation of the user of the motion tracking system, different physical exercises may have to be performed by the user. Some physical exercises may require the user to be in a certain way to perform certain movements. For instance, the physical exercise may require the user to lie on the floor with her/his back resting on the ground; in such posture, the user is unable to reach the computing apparatus in case she/he wants to configure the motion tracking procedure (e.g. pause it, stop it, resume it, etc.) or the physical rehabilitation activity (e.g. change to a different physical exercise, repeat the last physical exercise, etc.), thus the only way in which the user may operate the motion tracking system is by way of voice, otherwise the user would have to get up and reach any user input device(s) of the computing apparatus. Accordingly, as the predetermined flag is set such that it indicates that the user is not within reach of the computing apparatus (or user input devices thereof), the computing apparatus allows voice control irrespective of the SNR and the percentage of sensors computed. If the predetermined flag is set such that it indicates that the user is within reach of the computing apparatus (or user input devices thereof), the computing apparatus determines whether voice control is allowed or disallowed in accordance with the SNR and the percentage of sensors computed.

In some embodiments, the step of digitally processing the sound detected further comprises determining, from the sound detected, both existence of a voice command and the instruction of the voice command when it is determined that the voice command exists, and the method further comprising at least one of: digitally changing operation of the motion tracking system with the computing apparatus based on the instruction when the computing apparatus has last set allowance of voice control; and digitally maintaining same operation of the motion tracking system with the computing apparatus when the computing apparatus has last set disallowance of voice control.

The computing apparatus operates the motion tracking system in accordance with voice commands only when the voice control is allowed, otherwise it disregards the voice control even if it has been capable of determining the existence of the voice command and the instruction thereof. Preferably, when voice control is disallowed, the computing apparatus does not process the sound detected to determine what instructions are in voice commands so as not to waste computational resources and, thus, energy.

In some embodiments, the step of digitally setting allowance or disallowance further comprises at least one of: digitally providing or commanding provision of at least one perceptible signal indicative of allowance of voice control upon setting allowance of voice control; and digitally providing or commanding provision of at least one perceptible signal indicative of disallowance of voice control upon setting disallowance of voice control.

The perceptible signal(s) inform the user about the current configuration of the motion tracking system when it comes to voice control. Thanks to such signal(s), the user may take corrective action if desired and possible to have the computing apparatus allow voice control once again; for example, the user may move towards the computing apparatus, or attempt to turn off a source of noise that she/he may be aware of once informed by way of the signal(s).

In some embodiments, the method further comprises radiating, with each sensor of the plurality of sensors, electromagnetic waves having the data packets modulated therein.

A second aspect of the invention relates to a motion tracking system comprising:

a plurality of sensors adapted for arrangement on a body of a user and configured to wirelessly transmit data packets, each data packet including both a received signal strength indicator RSSI and one or more measurements of a respective sensor; and a computing apparatus comprising:
  at least one antenna;
  at least one microphone;
  at least one memory; and
  at least one processor configured to perform a method according to the first aspect of the invention.

The motion tracking system can be controlled by way of voice during those times when the computing apparatus configures the voice control to be allowed. The voice control is allowed when both the SNR resulting from the sound detected and the percentage of sensors that fulfill criteria concerning the distance between the sensors and the computing apparatus meet certain predetermined thresholds, otherwise the voice control is disabled.

In some embodiments, the motion tracking system or the computing apparatus further comprises one or more user input devices, e.g. keyboard, touchscreen, mouse, buttons, etc.

At least during those periods of time when the computing apparatus has disallowed voice control, the operation of the motion tracking system may be managed by means of the user input devices.

In some embodiments, the motion tracking system or the computing apparatus further comprises one or more presenting devices, e.g. one or more screens, LEDs, loudspeakers, vibrating devices, etc.

By way of the presenting devices, one or more perceptible signals may be provided for informing the user about the current configuration of voice control, i.e. whether it is allowed or not.

A third aspect of the invention relates to a computer program product that has instructions which, when executed by a computing apparatus, cause the computing apparatus to perform a method according to the first aspect of the invention. Preferably, the computing apparatus is a computing apparatus of a motion tracking system comprising a plurality of sensors adapted to be arranged on a body of a user, and the computing apparatus comprises at least one microphone and at least one antenna.

In some embodiments, the computer program product is embodied on a non-transitory computer readable medium.

A fourth aspect of the invention relates to a data stream which is representative of a computer program product according to the third aspect of the invention.

Similar advantages as those described for the first aspect of the invention are also applicable to the second, third and fourth aspects of the invention.

BRIEF DESCRIPTION OF THE DRAWINGS

To complete the description and in order to provide for a better understanding of the invention, a set of drawings is provided. Said drawings form an integral part of the description and illustrate embodiments of the invention, which should not be interpreted as restricting the scope of the invention, but just as examples of how the invention can be carried out. The drawings comprise the following figures.

DESCRIPTION OF WAYS OF CARRYING OUT THE INVENTION

Figure 1:
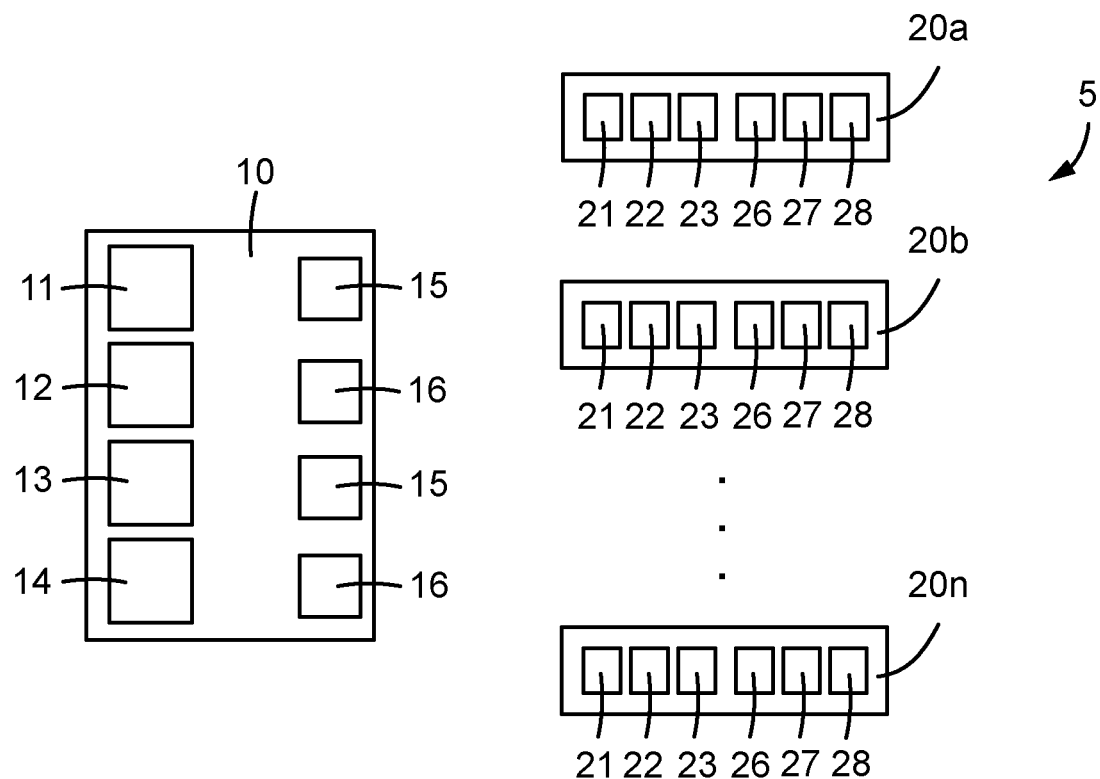
FIG. 1 diagrammatically shows a motion tracking system in accordance with an embodiment.

FIG. 1 diagrammatically shows a motion tracking system 5 in accordance with an embodiment. The motion tracking system 5 includes a plurality of sensors 20a-20n (e.g. two sensors, three sensors, four or even more sensors) and a computing apparatus 10, which may be e.g. a tablet, a mobile phone, a personal computer, etc.

Each sensor 20a-20n is adapted to be arranged on the body of a user so that the measurements provided by each sensor 20a-20n can be processed by the computing apparatus 10, thereby providing a motion sequence of the user. Each sensor 20a-20n is an inertial measurement unit that includes one or more sensing devices selected from: an accelerometer 21, a gyroscope 22 and a magnetometer 23. In the embodiment of FIG. 1, each sensor 20a-20n includes all three sensing devices 21-23. Preferably, all sensors 20a-20n include the same sensing devices 21-23.

The sensors 20a-20n further include at least one processor 26, at least one memory 27, and a first communications module 28 for transmitting data that enables the sensors to transmit RSSI values and measurements of the sensing device(s) 21-23 to the computing apparatus 10 through a wireless communications link (using a technology and protocol known by a skilled person, for instance but without limitation, Bluetooth and Bluetooth Low Energy communications, cellular network communications such as GSM, UMTS or LTE, wireless LAN communications, etc.). An antenna for radiating electromagnetic waves is provided as part of the first communications module 28. The same first communications modules 28, preferably, also enables the sensors 20a-20n to receive data from the computing apparatus 10 upon capturing electromagnetic waves with the antenna.

In some preferred embodiments, the at least one processor 26 of the sensors 20a-20n runs a sensor fusion algorithm for processing the measurements of the sensing devices 21-23 within the respective sensor. The sensor fusion algorithm is intended to enhance the raw measurements of the sensing devices by correcting errors thereof due to drifts of the sensing devices and, thus, outputs processed measurements that are to be transmitted to the computing apparatus 10.

The computing apparatus 10 includes at least one processor 11, at least one memory 12, and a second communications module 13 for at least receiving data. The computing apparatus 10 preferably also includes a screen 14 on which it shows the movements that are to be performed by an intended user of the motion tracking system 5 and feedback on the movements performed by the intended user during the motion tracking procedure. To this end, the computing apparatus 10 stores data relative to the physical exercises of intended users in the at least one memory 12. Any of these data can be transmitted to and/or received from another electronic device thanks to the second communications module 13. For example, a therapist is able to receive the feedback at a computing apparatus in a hospital so as to monitor the evolution of the person. Based on the feedback received, the therapist is able to adjust the difficulty of the movement(s), the number of repetitions thereof, prescribe new movements, etc. so that the person may further exercise using the motion tracking system 5. Further, in addition to the screen 14, which provides visual feedback, the computing apparatus 10 may also include further visual output means (e.g. LEDs, animations), audio output means (e.g. loudspeakers), vibrating means (e.g. a vibrator), etc. for providing user perceptible signals in the form of sounds, vibration, animated graphics, etc.

The computing apparatus 10 includes at least one antenna 15 whereby electromagnetic waves may be captured, and then processed with the second communications module 13 and the at least one processor 11. In the embodiment of FIG. 1, the computing apparatus 10 comprises two antennas 15, but in other embodiments the computing apparatus 10 is provided with one antenna, three antennas, or even more than three antennas.

Further, the computing apparatus 10 includes at least one microphone 16 whereby sound waves (i.e. pressure waves) may be detected, and then processed with the at least one processor 11. As it is readily apparent, the computing apparatus 10 includes analog-to-digital converters for digitizing detected sound waves and captured electromagnetic waves so that the streams of data may be processed by the at least one processor 11 and the second communications module 13. In the embodiment of FIG. 1, the computing apparatus comprises two microphones 16, but in other embodiments the computing apparatus 10 is provided with one microphone, or even more than two microphones.

Preferably, the computing apparatus 10 comprises a plurality of antennas 15 and a plurality of microphones 16 so that, whenever allowance of voice control is set, the computing apparatus 10 can carry out the procedure described in commonly owned European patent application EP19398014.1 so as to determine whether a voice command is coming from the user of the motion tracking system or not.

Figure 2:
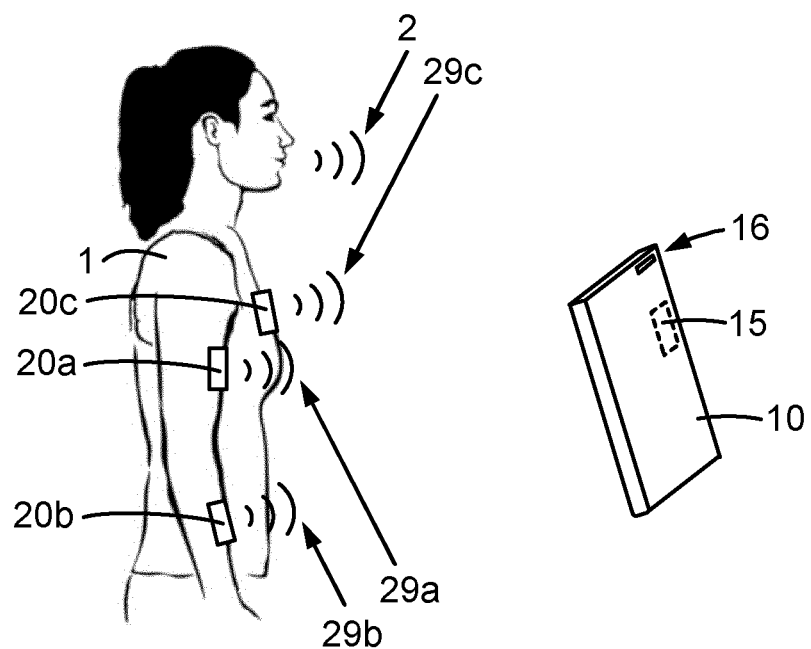
FIG. 2 shows a motion tracking system with sensors thereof arranged on a person.

FIG. 2 shows a motion tracking system with sensors 20a-20c thereof arranged on a person that is the user 1 of the system.

The user 1 has a first sensor 20a attached to the right upper arm, a second sensor 20b attached to the right lower arm, and a third sensor 20c attached to the chest. The sensors 20a-20c may be attached to the body of the user 1 in a number of ways, for instance using straps, Velcro, etc.

At a distance from the user 1 is a computing apparatus 10 of the motion tracking system. The computing apparatus 10 includes one microphone 16 and one antenna 15 (shown with dashed contours for illustrative purposes since antennas are typically within the housing of the computing apparatus 10).

Each of the sensors 20a-20c radiates electromagnetic waves 29a-29c whenever they are transmitting data packets in which they include measurements of the sensing devices and the RSSI thereof. The user 1 speaks and, thus, emits sound waves 2, for controlling the motion tracking system, thereby being able to operate the system without having to touch the computing apparatus 10. This is of great convenience because the user 1 is typically at a distance from the computing apparatus 10, e.g. one meter, two meters, five meters away, etc. whenever she/he is physically exercising. The microphone 16 picks up the sound waves 2, whereas the antenna 15 picks up the electromagnetic waves 29a-29c.

Figure 3:
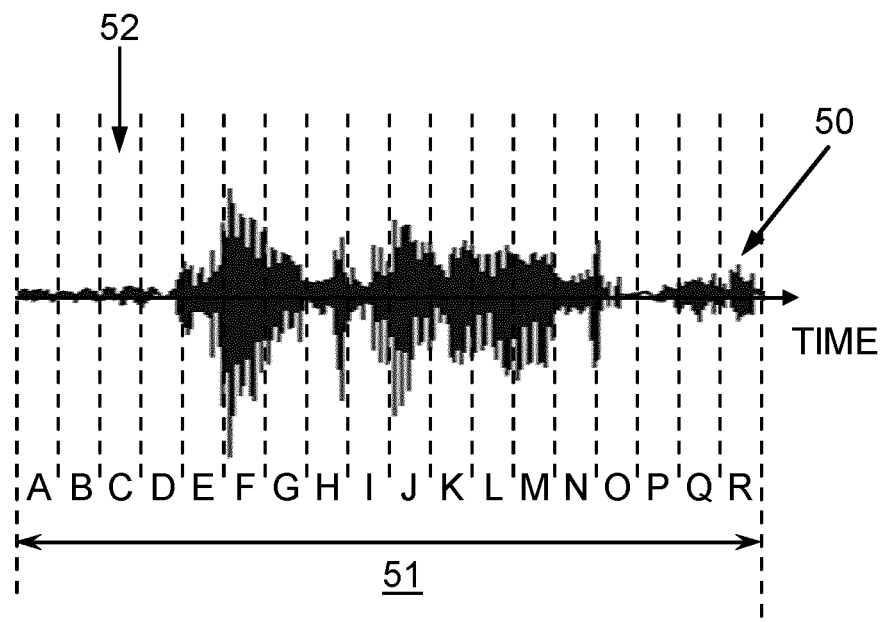
FIG. 3 shows sound detected with a microphone for processing thereof in order to compute SNR.

FIG. 3 shows sound 50 detected with a microphone for processing thereof in order to compute SNR.

The sound 50 is shown in a graph representing the time evolution of the sound 50 detected with a single microphone.

When the computing apparatus is provided with more than one microphone, a plurality of sound streams is detected, one stream per microphone.

In one embodiment, in order to calculate the SNR of the sound 50, a period of time 51 of the sound 50 is considered. From the period of time 51, a plurality of windows or frames 52 are digitally produced, each window or frame 52 includes a fragment of the sound 50 within the period of time 51. In this example, there are eighteen windows or frames 52 (from A to R), which are of equal duration, e.g. 25 ms.

The computing apparatus calculates the energy of all the windows or frames 52, and finds the one with highest energy, in this case the window or frame F. Then, the computing apparatus determines which windows or frames 52 are noise and which are voice; said determination is made by setting a minimum level of energy that it is assumed that voice will have, for which reason a percentage (e.g. 40%) of the energy of window F is computed. All the windows or frames 52 having an energy greater than that percentage, for example windows F, G, J, K, L and M are assumed to be voice, whereas the remaining windows or frames 52, which have an energy less than that percentage, are assumed to be noise.

The windows or frames 52 assumed to be noise are discarded for quantifying the energy of voice, that is to say, the energy of the non-discarded windows or frames 52 is considered to be the energy of signal, whereas the energy of the discarded windows or frames 52 is considered to be the energy of noise. With both values of energy, the SNR for the detected sound 50 is computed.

Figure 4:
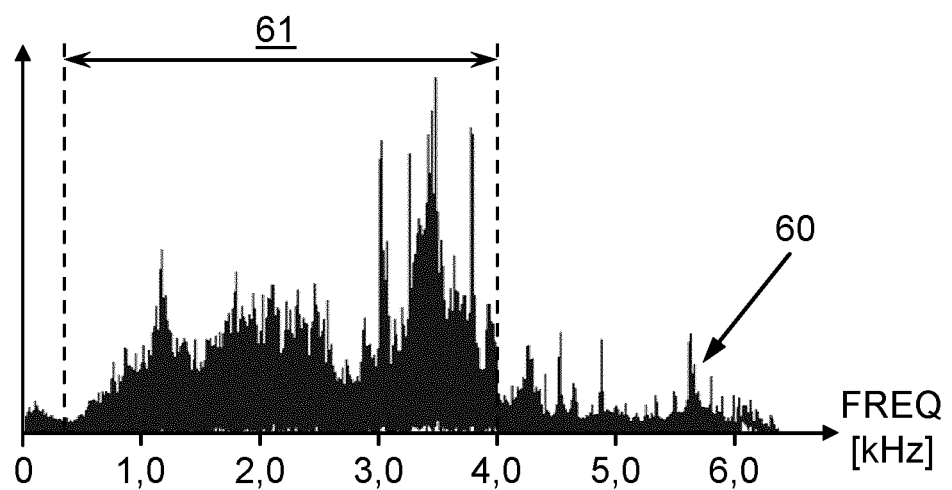
FIG. 4 shows a frequency spectrum of sound detected with a microphone for processing thereof in order to compute SNR.

FIG. 4 shows a frequency spectrum 60 of sound detected with a microphone for processing thereof in order to compute SNR.

In order to provide the frequency spectrum 60, the computing apparatus applies the FFT to a period of time of sound detected (for example, the sound 50 of FIG. 3) by each microphone.

Once the spectrum 60 is provided, the energy of voice can be computed over the frequency range 61 associated with human voice (e.g. from 0.3 kHz to 4.0 kHz), and the energy of noise can be computed over the remaining frequencies, i.e. those outside of frequency range 61.

In other embodiments, digital filters are applied to the sound detected, either in the time domain or in the frequency domain, such that one digital filter provides the sound for frequencies in the frequency range associated with human voice, and another digital filter provides the sound for frequencies not within said frequency range, thereby providing at least two sound streams for voice and noise in the time or frequency domains. From these at least two sound streams, the energy of voice and noise may be computed.

Figure 5:
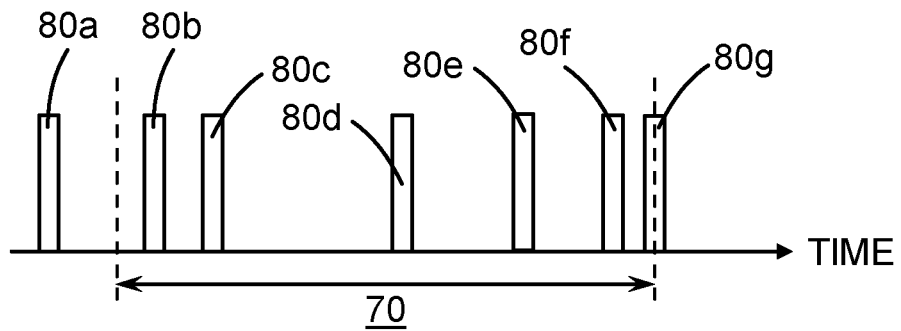
FIG. 5 diagrammatically shows reception of data packets at a computing apparatus.

FIG. 5 diagrammatically shows reception of data packets 80a-80g at a computing apparatus.

The reception of data packets 80a-80g is shown over time upon capturing the corresponding electromagnetic waves with one or more antennas of the computing apparatus. The data packets 80a-80g shown correspond to a same sensor out of the plurality of sensors, thus for each sensor a similar graph can be provided.

The computing apparatus processes the data packets 80a-80g so as to retrieve the one or more measurements and the RSSI included therein. Based on the RSSI values, the computing apparatus computes the distance at which the sensor is from the computing apparatus. In this sense, the computing apparatus may also compute a change in the distance computed as the data packets 80a-80g are received, the mean distance between the sensor and the computing apparatus, and the change in mean distance.

For computing the change in distance, for example, the computing apparatus establishes a time interval 70 according to which it may determine how the distance has changed. In this case, the computing apparatus determines the change in distance by computing the distance based on the RSSI values of each data packet 80$b$-80$f$ within the time interval 70 (the last data packet 80$g$ has not arrived completely within the time interval 70 under evaluation, whereas the first data packet 80$a$ has arrived before the start of the time interval 70 under evaluation, thus both data packets 80$a$, 80$g$ are not considered in this computation). Then, it may compare the change in distance between any pair of the calculated values with e.g. max_change_dist as long as the time difference between the reception of the pair of data packets does not exceed e.g. max_change_dist_time.

Likewise, the computing apparatus can compute the mean distance by averaging the distance values computed from the different data packets 80$b$-80$f$ within the time interval 70, which should at least be of duration e.g. min_distance_time but not more than e.g. max_distance_time.

By computing the mean distances as the different data packets arrive, the computing apparatus may then compute change in mean distance, which is carried out similarly: the time interval 70 in that case extends between e.g. min_mean_distance_time and e.g. max_mean_distance_time, and the mean distances (computed as explained above) compared must have been calculated such that the last data packet considered for the corresponding mean distance is encompassed by said time interval.

In each of these cases, the distance, mean distance, change in distance, or change in mean distance is calculated for each sensor, and then the computing apparatus computes the percentage of sensors exceeding or not exceeding the threshold corresponding to that calculation. Then, the computing apparatus sets allowance or disallowance of voice control depending upon whether the percentage of thresholds exceeds e.g. max_sensor_perc, and also depending upon the SNR values calculated as described, for example, with reference to FIGS. 3-4.

Figure 6:
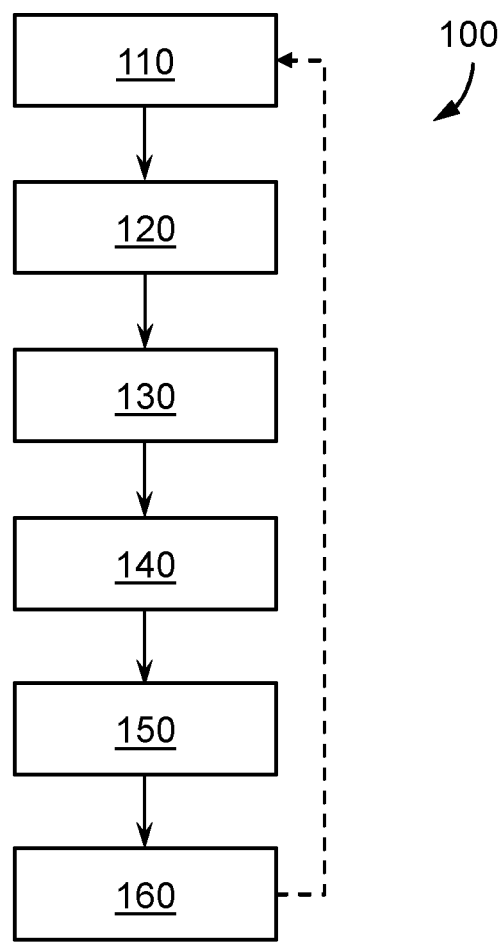
FIG. 6 diagrammatically shows a method in accordance with an embodiment.

FIG. 6 diagrammatically shows a method 100 for allowing or disallowing control of a motion tracking system (for example, the motion tracking system 5 of FIG. 1) by means of voice in accordance with an embodiment.

The method 100 comprises a step 110 whereby a computing apparatus (for example, the computing apparatus 10 of any one of FIGS. 1-2) of the motion tracking system processes sound waves detected by the at least one microphone.

The method 100 further comprises a step 120 whereby the computing apparatus processes the detected sound and computes a signal-to-noise ratio. In order to compute the signal-to-noise ratio, the computing apparatus computes both the energy of voice in the detected sound, and the energy of noise in the detected sound.

When the computing apparatus comprises more than one microphone, the sound is detected through each microphone and preferably each stream of sound of the different microphones is processed independently from the other(s) so as to compute the SNR for each stream of sound.

The method 100 further comprises a step 130 whereby the computing apparatus processes electromagnetic waves captured by the at least one antenna so as to detect data packets in the electromagnetic waves. The electromagnetic waves are radiated by sensors (for example, the sensors 20$a$-20$n$ of any one of FIGS. 1-2) of the motion tracking system such that data packets can be transmitted to the computing apparatus. The sensors include measurements thereof in the data packets and received signal strength indicator values.

The method 100 further comprises a step 140 whereby the computing apparatus computes a distance between each sensor and the computing apparatus using the RSSI values in the data packets processed 130. Likewise, when several data packets from a same sensor are received, the computing apparatus can compute, owing to the different RSSI values, a mean distance, a change in distance and/or a change in mean distance.

The method 100 further comprises a step 150 whereby the computing apparatus computes a percentage of sensors of the plurality of sensors that have at least one of: a distance exceeding a predetermined maximum distance threshold, and a change in distance exceeding a predetermined maximum changing distance threshold. The distances and changes in distance are those computed 140 by the computing apparatus based on the RSSI values in the data packets.

The steps 130, 140 and 150 corresponding to detection of data packets, the calculation of distances (or changes in distances), and the calculation of the percentage of sensors, may take place prior to any one of the steps 110 and 120 corresponding to the detection of sound and calculation of SNR, or both processes may be carried out in parallel.

Preferably, the computing apparatus processes 110 sound whenever the at least one microphone detects it, and processes 130 electromagnetic waves whenever the at least one antenna captures them, in this way the adjustments to the operation of the motion tracking system take less time.

The method 100 further comprises a step 160 whereby the computing apparatus digitally sets allowance or disallowance of voice control based on both the SNR computed 120 and the percentage of sensors computed 150.

When the computing apparatus comprises more than one microphone, the SNRs for each stream of sound as computed in step 120 are preferably averaged and the mean SNR is used for digitally setting 160 allowance or disallowance of voice control. Alternatively, the computing apparatus can digitally set 160 allowance or disallowance of voice control based on each computed SNR, in which case preferably all the SNRs shall exceed a predetermined minimum SNR threshold and the percentage of sensors computed shall not exceed a predetermined maximum distant sensors threshold for allowing voice control.

In preferred embodiments, the method 100 further comprises a step 170 whereby the computing apparatus repeats the described process so that the allowance or disallowance of voice control may be digitally set 160, for example during an entire physical exercising session of a user.

In this text, the terms first, second, third, etc. have been used herein to describe several devices, elements or parameters, it will be understood that the devices, elements or parameters should not be limited by these terms since the terms are only used to distinguish one device, element or parameter from another. For example, the first energy could as well be named second energy, and the second energy could be named first energy without departing from the scope of this disclosure.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A method for allowing or disallowing control of a motion tracking system by means of voice, the motion tracking system comprising a plurality of sensors adapted for arrangement on a body of a user and to wirelessly transmit data packets, and a computing apparatus to receive the data packets, wherein each of the sensors includes at least one inertial measurement device and a first communications module with an antenna, and wherein the computing apparatus comprises at least one processor, a second communications module, at least one antenna and at least one microphone, the method comprising:
digitally processing, with the computing apparatus, sound detected by each microphone of the at least one microphone;
digitally computing, with the computing apparatus, a signal-to-noise ratio by computing both first energy of a voice signal in the detected sound and second energy of noise in the detected sound;
digitally processing, with the computing apparatus, electromagnetic waves captured by each antenna of the at least one antenna so as to detect data packets transmitted to the computing apparatus by each sensor of the plurality of sensors, each data packet including both a received signal strength indicator RSSI and one or more measurements of a respective sensor, the RSSI being indicative of strength with which the respective sensor receives a wireless signal from the computing apparatus;
digitally computing, with the computing apparatus, distance between each sensor and the computing apparatus based on the RSSI of the data packets received from the respective sensor;
digitally computing, with the computing apparatus, a percentage of sensors of the plurality of sensors having at least one of: a distance exceeding a predetermined maximum distance threshold, or a change in distance exceeding a predetermined maximum changing distance threshold; and
digitally setting, in the computing apparatus, allowance or disallowance of voice control based on both the SNR computed and the percentage of sensors computed.

2. The method of claim 1, wherein digitally setting allowance or disallowance comprises: allowing voice control when both the SNR computed exceeds a predetermined minimum SNR threshold and the percentage of sensors computed does not exceed a predetermined maximum distant sensors threshold; and disallowing voice control when the SNR computed does not exceed the predetermined minimum SNR threshold or the percentage of sensors computed exceeds the predetermined maximum distant sensors threshold.

3. The method of claim 1, wherein the distance between each sensor and the computing apparatus digitally computed is a mean distance between each sensor and the computing apparatus in a time interval having a duration between a predetermined minimum distance time threshold and a predetermined maximum distance time threshold.

4. The method of claim 3, wherein the percentage of sensors is a ratio of A divided by B, where A is a number of sensors whose computed mean distance has increased more than a predetermined maximum mean distance change threshold in a time interval having a duration between a predetermined minimum mean distance time threshold and a predetermined maximum mean distance time threshold, and B is a total number of sensors in the plurality of sensors.

5. The method of claim 1, wherein the computed distance between a sensor and the computing apparatus is either equal to or proportional to $$10^{\frac{Pmeasured - RSSImean}{10 \cdot K}},$$

where Pmeasured is a predetermined value corresponding to expected power with which an antenna captures electromagnetic waves of the sensors at a predetermined distance value from the computing apparatus, RSSImean is a mean RSSI of the corresponding sensor, and K is a predetermined value corresponding to a factor of wave propagation in an environment where the motion tracking system is located.

6. The method of claim 1, wherein digitally computing the SNR comprises: providing a plurality of time windows, each time window comprising a different fragment of sound detected; computing energy of the sound in each time window of the plurality of time windows; setting a maximum energy value with the highest computed energy; discarding the time windows of the plurality of time windows having energy less than a predetermined percentage of the highest computed energy; and computing the first energy based on the non-discarded time windows of the plurality of time windows, and the second energy based on the discarded time windows of the plurality of time windows.

7. The method of claim 6, wherein each time window has a same time duration.

8. The method of claim 1, wherein digitally computing the SNR comprises P1 or P2, wherein P1 comprises: transforming the sound detected into a frequency domain; computing the first energy of the sound detected for frequencies within a frequency range associated with human voice; and computing the second energy of the sound detected for frequencies different from the frequency range associated with human voice; and wherein P2 comprises: applying at least a first digital filter to the sound detected thereby providing a first filtered sound, the first digital filter being a bandpass filter for frequencies of the frequency range associated with human voice; applying at least a second digital filter to the sound detected thereby providing a second filtered sound, the second digital filter at least filtering out frequencies of the frequency range associated with human voice; and computing the first energy from the first filtered sound and the second energy from the second filtered sound.

9. The method of claim 1, further comprising repeating the digital operations of the method with the computing apparatus one or more times for digitally setting allowance or disallowance of voice control in accordance with both most recent sound detection and most recent electromagnetic wave capture.

10. The method of claim 1, wherein digitally setting allowance or disallowance is further based on a predetermined flag corresponding to a physical exercise to be carried out by the user such that: when the predetermined flag is indicative of the user not being within reach of the computing apparatus during performance of the physical exercise, the computing apparatus digitally sets allowance of voice control irrespective of both the SNR computed and the percentage of sensors computed; and when the predetermined flag is indicative of the user being within reach of the computing apparatus during performance of the physical exercise, the computing apparatus digitally sets allowance or disallowance based on both the SNR computed and the percentage of sensors computed.

11. The method of claim 1, wherein digitally processing the sound detected further comprises determining, from the sound detected, both existence of a voice command and an instruction of the voice command when it is determined that the voice command exists, and the method further comprising at least one of: digitally changing operation of the motion tracking system with the computing apparatus based on the instruction when the computing apparatus has last set allowance of voice control; or digitally maintaining same operation of the motion tracking system with the computing apparatus when the computing apparatus has last set disallowance of voice control.

12. The method of claim 1, wherein digitally setting allowance or disallowance further comprises at least one of: digitally providing or commanding provision of at least one perceptible signal indicative of allowance of voice control upon setting allowance of voice control; or digitally providing or commanding provision of at least one perceptible signal indicative of disallowance of voice control upon setting disallowance of voice control.

13. The method of claim 1, wherein digitally computing distance between each sensor and the computing apparatus based on the RSSI of the data packets received from the respective sensor comprises establishing the distance according to the RSSI of the data packets.

14. A motion tracking system comprising: a plurality of sensors adapted for arrangement on a body of a user and to wirelessly transmit data packets, each of the sensors includes at least one inertial measurement device, and a first communications module with an antenna, each data packet including both a received signal strength indicator RSSI and one or more measurements of a respective sensor, the RSSI being indicative of strength with which the respective sensor receives a wireless signal from a computing apparatus; and the computing apparatus comprising: a second communications module; at least one antenna; at least one microphone; at least one memory; and at least one processor to perform the method of claim 1.

15. A computer program product comprising a non-transitory computer readable medium storing instructions which, when executed by a computing apparatus, cause the computing apparatus to perform the method of claim 1.

* * * * *